(12) United States Patent
Goodwin et al.

(10) Patent No.: US 10,209,175 B2
(45) Date of Patent: Feb. 19, 2019

(54) DETECTION OF CORROSION USING DISPERSED EMBEDDED SENSORS

(71) Applicant: MICROSS ADVANCED INTERCONNECT TECHNOLOGY LLC, Durham, NC (US)

(72) Inventors: Scott Goodwin, Chapel Hill, NC (US); Mark Roberson, Cary, NC (US); John Lewis, Durham, NC (US); Dorota Temple, Cary, NC (US)

(73) Assignee: Micross Advanced Interconnect Technology LLC, Durham, NC (US)

( * ) Notice: Subject to any disclaimer, the term of this patent is extended or adjusted under 35 U.S.C. 154(b) by 199 days.

(21) Appl. No.: 15/223,346

(22) Filed: Jul. 29, 2016

(65) Prior Publication Data

US 2017/0030825 A1    Feb. 2, 2017

Related U.S. Application Data

(60) Provisional application No. 62/199,584, filed on Jul. 31, 2015.

(51) Int. Cl.
*G01N 17/04*    (2006.01)
*G01N 29/02*    (2006.01)
*G01N 11/16*    (2006.01)

(52) U.S. Cl.
CPC .................................... *G01N 17/04* (2013.01)

(58) Field of Classification Search
CPC ..................................................... G01N 17/04
See application file for complete search history.

(56) References Cited

U.S. PATENT DOCUMENTS

| 4,560,275 A | 12/1985 | Goetz |
| 5,475,221 A | 12/1995 | Wang |
| 5,519,219 A | 5/1996 | Alexay et al. |
| 6,043,893 A | 3/2000 | Treiman et al. |

(Continued)

FOREIGN PATENT DOCUMENTS

WO    2014022705 A1    2/2014

OTHER PUBLICATIONS

Boreman, Glenn D.; :Infrared Antennas & Frequency Selective Surfaces CREOL, The College of Optics & PhotonicsUniversity of Central Florida Orlando, FL; Apr. 29, 2011.

(Continued)

*Primary Examiner* — Huy Q Phan
*Assistant Examiner* — Zannatul Ferdous
(74) *Attorney, Agent, or Firm* — Olive Law Group, PLLC

(57) ABSTRACT

A corrosion sensor system includes one or more corrosion sensors embedded in a coating material such as an anti-corrosion coating material. Each corrosion sensor may include a resonator disposed on a dielectric substrate, and has a resonant frequency in a radio frequency (RF) range or an infrared (IR) range, and is configured for interacting with an RF or IR excitation signal to produce an RF or IR measurement signal. The corrosion sensor system may be applied to an object for which corrosion is to be monitored. A corrosion detection system includes a data acquisition system that transmits the excitation signal to the corrosion sensor, and receives the measurement signal from the corrosion sensor for analysis to determine whether corrosion has occurred.

29 Claims, 8 Drawing Sheets

(56) References Cited

U.S. PATENT DOCUMENTS

| | | | |
|---|---|---|---|
| 2003/0132760 A1* | 7/2003 | Bray | G01N 17/00 324/637 |
| 2005/0135546 A1* | 6/2005 | Ponstingl | G01N 21/55 376/305 |
| 2011/0285942 A1* | 11/2011 | Guo | G02B 5/008 349/96 |
| 2014/0182363 A1* | 7/2014 | Potyrailo | G01N 27/026 73/64.53 |

OTHER PUBLICATIONS

Puscau and W.L. Schaich, Appl Phys Lett, 92, 233102 (2008).

* cited by examiner

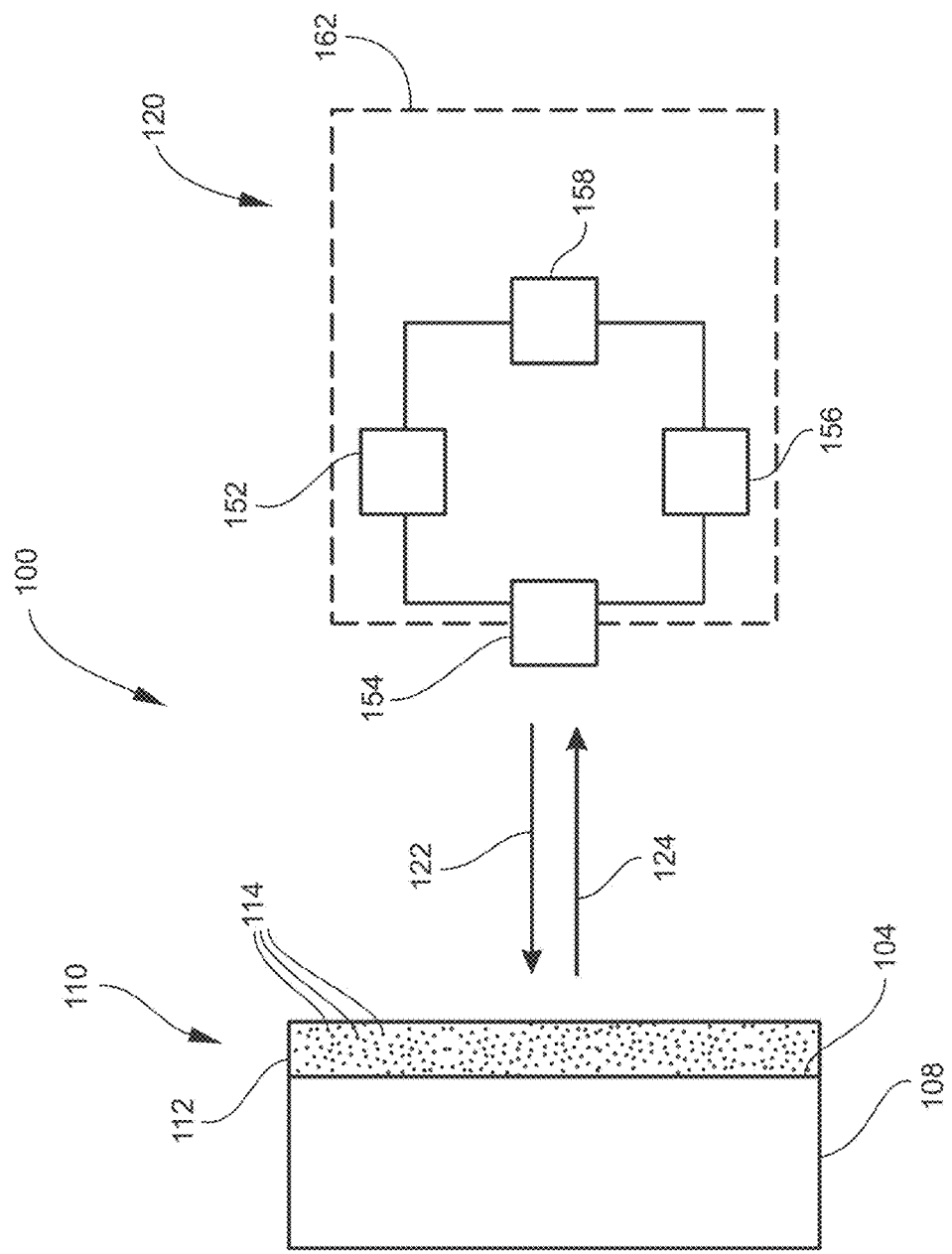

DETECTION OF CORROSION USING DISPERSED EMBEDDED SENSORS

RELATED APPLICATIONS

This application claims the benefit of U.S. Provisional Patent Application No. 62/199,584, filed Jul. 31, 2015, titled "DETECTION OF CORROSION USING DISPERSED EMBEDDED SENSORS," the content of which is incorporated by reference herein in its entirety.

TECHNICAL FIELD

The present invention relates generally to detection of corrosion, and more particularly to detection of corrosion utilizing sensors embedded in a material such a coating applied to an object susceptible to corrosion.

BACKGROUND

Corrosion generally refers to an electrochemical process by which a metal is converted to metal oxides. Corrosion is destructive to metallic articles of manufacture and therefore is undesirable. To prevent or slow down the process of corrosion, an anti-corrosion (corrosion-resistant) coating may be applied to the outer surface of a metal, i.e., the surface exposed to the environment. Generally an anti-corrosion coating is, or includes, a formulation effective for resisting degradation due to moisture, salt, oxidation, or chemical exposure. Anti-corrosive behavior provides additional protection in altering the fundamental mechanisms for corrosion, in addition to slowing them down. The adequate function of such coatings is critical, as premature failure of valuable articles of manufacture due to corrosion can have significant financial consequences as well as pose safety risks in the case of objects providing structural support. Therefore, for many types of metal objects, it is desirable to monitor corrosive activity to facilitate the ability to take remedial action as needed and on a timely basis. Anti-corrosion coatings, however, are not inherently capable of monitoring corrosive activity.

Therefore, it would be desirable to add functionality to anti-corrosion coatings and other types of coatings that enables the monitoring and early detection of corrosion. Such functionality could provide a significant value-added feature that could save time and money for the end user and, depending on the type of metal article involved, promote safety measures such as by enhancing the prevention of catastrophic structural failure.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a corrosion sensor system includes: a coating material; and a corrosion sensor embedded in the coating material, the corrosion sensor comprising a dielectric substrate and a resonator disposed on the dielectric substrate, wherein: the coating material, the dielectric substrate, and the resonator define a resonant frequency of the corrosion sensor in a radio frequency (RF) range or an infrared (IR) range; and the resonator is configured for interacting with an RF or IR excitation signal to produce an RF or IR measurement signal.

According to another embodiment, the corrosion sensor system includes a plurality of corrosion sensors dispersed throughout the coating material.

According to another embodiment, a corrosion detection system includes: one or more corrosion sensors; and a data acquisition system comprising an RF or IR excitation signal source, a transceiver configured for transmitting an excitation signal to one or more of the corrosion sensors and for receiving a measurement signal from one or more of the corrosion sensors, and an RF or IR signal analyzer configured for analyzing the measurement signal.

In some embodiments, the corrosion sensor has a baseline resonant frequency corresponding to an absence of corrosion in a sensing region proximate to and surrounding the corrosion sensor, and the signal analyzer is configured for: measuring a wavelength or frequency spectrum of the measurement signal; finding a peak or notch wavelength or frequency of the measured spectrum; based on the peak or notch wavelength or frequency, calculating an actual resonant frequency of the corrosion sensor; and determining whether corrosion has occurred in the sensing region based on a difference between the baseline resonant frequency and the actual resonant frequency.

In some embodiments, the wavelength or frequency spectrum comprises RF signal magnitude as a function of wavelength or frequency, IR reflectance as a function of wavelength, or IR emission as a function of wavelength.

According to another embodiment, a method for detecting corrosion of an object includes: transmitting an RF or IR excitation signal whose wavelength or frequency vary in a predetermined range to a corrosion sensor embedded in a coating material disposed on the object, wherein the corrosion sensor has a baseline resonant frequency corresponding to an absence of corrosion in a sensing region proximate to and surrounding the corrosion sensor, and detecting any change in the measured response of the corrosion sensor to receiving the RF or IR excitation signal; measuring a wavelength-dependent parameter of the measurement signal; based on the measured parameter, calculating an actual resonant frequency of the corrosion sensor; and determining whether corrosion has occurred in the sensing region based on a difference between the baseline resonant frequency and the actual resonant frequency.

According to another embodiment, a corrosion detection system is configured for performing any of the methods disclosed herein.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIG. 1 is a schematic view of an example of a corrosion detection system according to some embodiments.

DETAILED DESCRIPTION

Figure 2A:
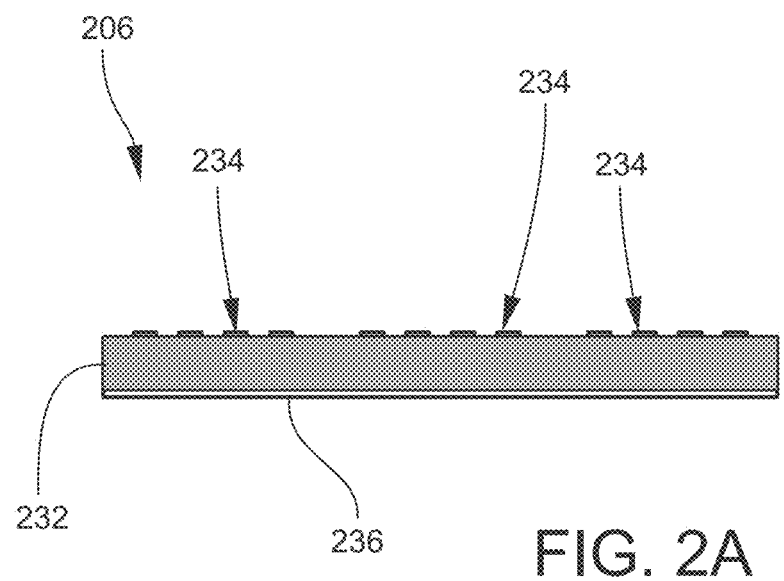
FIG. 2A is a schematic side view of an example of a wafer-level structure that may be fabricated as part of fabricating corrosion sensors according to some embodiments.

According to an aspect of the present disclosure, a corrosion sensing system is provided. The corrosion sensing system is formed by embedding one or more corrosion sensors in a coating material (or, more simply, a "coating"). The corrosion sensing system may be applied as a coating to the surface of any object for which corrosion sensing is desired. As described further below by way of non-limiting examples, the corrosion sensors are electromagnetic devices operating in, or sensitive to wavelengths/frequencies in, the radio frequency (RF) or infrared (IR) spectrum. The corrosion sensors are configured for interacting with received electromagnetic (RF or IR) excitation signals to produce electromagnetic (RF or IR) measurement signals. The corrosion sensors may be passive devices, powered only by incident excitation signals. The measurement signal or signals produced by a corrosion sensor may be analyzed to determine whether corrosion has occurred (or is occurring) in the vicinity (sensing region) of that corrosion sensor.

The corrosion sensing system may be considered as a composite or suspension of one or more corrosion sensors and a coating. The coating serves as a matrix supporting the corrosion sensor, or dispersion of multiple corrosion sensors, in proximity to the object for which corrosion is being monitored. The coating surrounding each corrosion sensor also influences the resonant frequency of that corrosion sensor, thereby enabling corrosion sensing as described further below. The coating may serve other, more conventional functions as described below. Thus, embodiments disclosed herein add a functionality to coatings that enables the monitoring and early detection of corrosion. This corrosion-sensing functionality is integral to the coating itself rather than, for example, being a discrete patch that is part of the coated object. The corrosion sensors are chemically inert structures and thus their addition to the coating does not appreciably modify the coating. Moreover, the addition of the corrosion sensors does not appreciably modify the process for coating the object. As such, the corrosion-sensing functionality resulting from adding the corrosion sensors involves minimal interaction with the coating itself, and thus avoids unintended consequences that might result from modifying the coating or the coating process. Moreover, as the corrosion sensors receive excitation signals and transmit measurement signals wirelessly, the corrosion-sensing functionality imparted to the coating is measurable noninvasively, i.e., without contact with or damage to the coating or the object. In addition, the interrogation process (i.e., transmitting excitation signals to and measuring response signals from the corrosion sensors) may be done without specialized training. Likewise, the data encoded in the measurement signals may be easily interpreted without specialized training, such as by providing an appropriate data acquisition system according to some embodiments disclosed herein. The corrosion-sensing functionality may be sufficiently sensitive to detect corrosion prior to excessive damage, or in some embodiments even before the onset of corrosion.

In typical embodiments, multiple corrosion sensors are dispersed throughout the coating. The number and density of corrosion sensors included in a given volume of coating may vary from one application to another. The number and density of corrosion sensors may depend in part on factors such as, for example, the size of the surface area of the object covered by the coating (i.e., the area over which corrosion sensing is desired), and the size of the effective sensing region surrounding each corrosion sensor (i.e., the sensing limit of the corrosion sensor, or the spatial range in which corrosion sensing by the corrosion sensor is effective). In some embodiments, the size of the corrosion sensor is on the scale of micrometers ($\mu m$). Thus in a given application, a corrosion sensing system as disclosed herein, after being applied to an object, may potentially include thousands or millions of individual corrosion sensors distributed throughout the coating. The size of the corrosion sensor may be defined by the maximum spatial dimension of the corrosion sensor, which is in turn defined by its shape. The corrosion sensor may, for example, have a polygonal (prismatic) shape (e.g., a chip), in which case the maximum spatial dimension may be the length of a side of the corrosion sensor. Alternatively, the corrosion sensor may be shaped as a disk, in which case the maximum spatial dimension may be the diameter of the disk. As examples, the maximum spatial dimension of the corrosion sensor may be 1000 $\mu m$ or less (e.g., 1 $\mu m$ to 1000 $\mu m$), or 500 $\mu m$ or less, or 100 $\mu m$ or less, or 50 $\mu m$ or less. As additional examples, the maximum spatial dimension of the corrosion sensor may be in a range from 5 $\mu m$ to 50 $\mu m$, or from 5 $\mu m$ to 20 $\mu m$, or from 5 $\mu m$ to 10 $\mu m$.

In the context of the present disclosure, a "coating" or "coating material" generally refers to any material that may be applied to the surface of an object so as to cover or "coat" that surface in a permanent manner and thereby form a barrier between the surface and the environment. As examples, a coating may be a layer or film of material disposed on a surface. Generally, no limitations are placed on the composition, thickness, properties, function or intended use of the coating. The coating may be transparent, translucent, or opaque. In some embodiments, the coating is an anti-corrosion coating. Examples of anti-corrosion coatings include, but are not limited to, epoxy, polyurethane, strontium chromate, and zinc phosphate. Alternatively, the coating may be any other type of coating applied to a surface. As one example, the coating may be a paint or ink intended to impart a color to the object, i.e., a coating containing a colorant such as a pigment or dye. Alternatively or additionally, the coating may be formulated to impart other types of optical properties to a surface, such as to enhance or suppress reflectivity or gloss level.

Generally, the corrosion sensing system may be fabricated by any process that involves adding one or more corrosion sensors to a quantity of coating material. In some embodiments, the coating is fabricated in a manner conventional for its type. For example, an anti-corrosion coating may be fabricated using a known process for fabricating anti-corrosion coatings. In some embodiments, the coating is provided in a prefabricated form, i.e., as a commercially available or commercial off-the-shelf (COTS) product. After the coating has been provided (fabricated on-site or acquired off-the-shelf), the corrosion sensors may be added generally in any fashion that does not damage or alter the corrosion sensors, such as by operating an appropriate dispensing apparatus. After so forming the corrosion sensing system, the corrosion sensing system may be applied as a coating (e.g., in the manner of a conventional coating) to any object for which corrosion sensing is desired. The corrosion sensing system may be applied to the object in any manner, for example, spraying, dipping, spinning on, printing, painting, etc. The corrosion sensing system may initially be provided in a liquid or other flowable form, with the corrosion sensors suspended in the matrix of the coating material. The manner in which the coating material adheres or bonds to the surface in a permanent manner may generally depend on the type of coating material. After being applied to the object, the mechanism by which the coating material sets into a permanent, solid form on the object (e.g., drying, curing, cross-linking, etc.) may likewise generally depend on the on the type of coating material. Prior to applying the corrosion sensing system, the system may if needed or desired be physically perturbed (e.g., tumbled, agitated, etc.) to promote or enhance the distribution of the corrosion sensors throughout the bulk of the coating material.

FIG. 1 is a schematic view of an example of a corrosion detection system 100 according to some embodiments. The corrosion detection system 100 may generally include a corrosion sensing system 110 and a data acquisition system 120. As described above, the corrosion sensing system 110 includes a coating material 112 and a plurality of corrosion sensors 114 dispersed in the coating material 112, i.e., embedded in the coating material 112 in a distributed manner. FIG. 1 illustrates the corrosion sensing system 110 after it has been applied to a surface 104 of an object 108 to be monitored for corrosion. In other embodiments, particularly very small-scale applications, the corrosion sensing system 110 may include just a single corrosion sensor 114 or a few corrosion sensors 114. In operation, the data acquisition system 120 communicates with the corrosion sensors 114 via RF or IR excitation signals 122 and RF or IR measurement signals 124, as described further below.

In some embodiments, the configuration and operation of the corrosion sensors 114 are based on the observation that corrosive activity at the object surface 104 leads to compositional changes in the coating material 112, which in turn alters one or more electrical properties of the coating material 112 such as conductivity, dielectric properties, etc. In such embodiments, the corrosion sensors 114 each are configured to output a measurement signal that may be received by the data acquisition system 120 and decoded so as to determine whether a change in an electrical property is indicative of the occurrence of corrosion within the sensing region of the corrosion sensor 114. For this purpose, the corrosion sensor 114 may be modeled as a distributed-element or lumped-element RLC circuit (with a characteristic resistance, inductance, and capacitance) having a resonant frequency and responsive to RF wavelengths. Such a corrosion sensor 114, when initially integrated into the coating material 112 and when the resulting corrosion sensing system 110 is initially applied to the object 108, has an initial or baseline resonant frequency and quality factor (Q factor, or simply Q) corresponding to the absence of corrosion in the sensing region. In the present context, the quality factor Q may be defined as ratio of the resonant frequency ($f_r$) to the bandwidth ($\Delta f$) of the resonator of the corrosion sensor 114. When the corrosion sensor 114 is integrated into the coating material 112, the corrosion sensor 114 in effect integrates the surrounding volume (sensing region) of the coating material 112 as a "parasitic" component of the RLC circuit. Hence, the resonant frequency and the Q of the RLC circuit depend at least in part upon the electrical properties of the coating material 112, such that a subsequent change in one or more electrical properties of the coating material 112 due to corrosive activity will result in a change, or shift, in the resonant frequency and/or the Q of the RLC circuit. An indication of a change in resonant frequency (i.e., one or more measurable electrical properties) is encoded in the measurement signal outputted by the corrosion sensor 114. The data acquisition system 120 may be configured to analyze the signature of the measurement signal in a manner that determines whether the resonant frequency and/or the Q of the corrosion sensor 114 has shifted, and whether such shift is indicative of corrosion. The data acquisition system 120 may be configured to detect and quantify a shift in resonant frequency and/or the Q by, for example, comparing the measured or calculated resonant frequency and/or the Q with the known baseline resonant frequency and/or the Q of the corrosion sensor 114. As the coating material 112 surrounding the corrosion sensor 114 affects the electrical properties of the corrosion sensor 114 such as resonant frequency and Q factor, such electrical properties may be considered as being associated with the overall corrosion sensing system 110 (i.e., the corrosion sensor 114 embedded in the coating material 112).

In some embodiments, the corrosion sensor 114 includes a dielectric substrate and a resonator disposed on the dielectric substrate. The resonator has a resonant frequency in the RF range, and is configured for interacting with an RF excitation signal. The resonant frequency of the corrosion sensor 114 may be dictated in part by the dimensions of the features of the resonator. As noted above, in some embodiments the corrosion sensor 114 may have micrometer-scale dimensions. Such a corrosion sensor 114 may be fabricated according to techniques known in the fields of microelectronics and/or microelectromechanical systems (MEMS). The corrosion sensor 114 may be formed as a planar chip (or chiplet) with a thickness defined between opposing planar sides. The cross-section of the planar sides may be polygonal or rounded. The resonator and the dielectric substrate may be arranged as (or similar to) an RF transmission line or as discrete L/C components. For example, the corrosion sensor 114 may have a planar geometry similar to a microstrip or stripline transmission line. The resonator, the dielectric substrate, and the surrounding coating material may together define the resonant frequency, Q factor, and other electrical properties of the corrosion sensor 114.

FIGS. 2A to 4 illustrate non-limiting examples of an RF corrosion sensor according to some embodiments.

Figure 2B:
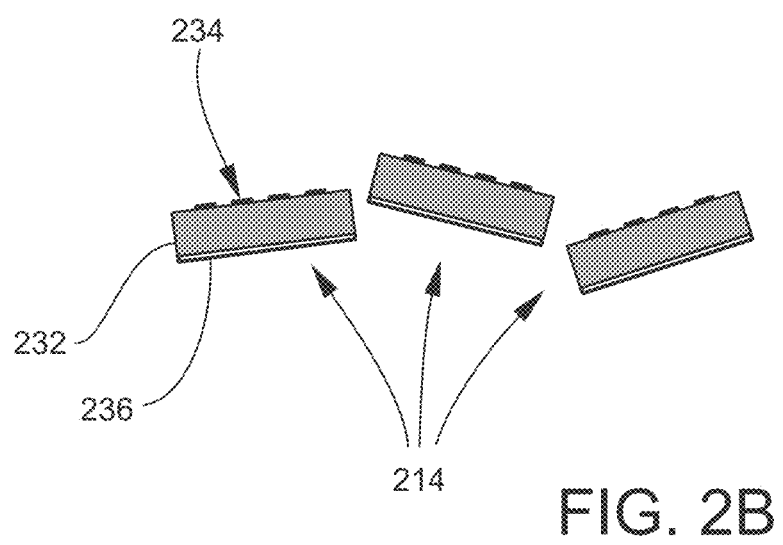
FIG. 2B is a schematic side view of an example of multiple die cut from the wafer-level structure illustrated in FIG. 2A.

FIGS. 2A and 2B illustrate an example of fabricating RF corrosion sensors 214 by implementing a wafer-level microelectronic fabrication process. Specifically, FIG. 2A is a schematic side view of an example of a wafer-level structure 206, and FIG. 2B is a schematic side view of an example of multiple die cut from the wafer-level structure 206. Referring to FIG. 2A, a wafer-sized dielectric substrate 232 is provided. Generally, the dielectric substrate 232 may be composed of any dielectric material suitable for high-frequency (RF) transmission. A metallization layer is deposited on a first side (top side, from the perspective of FIG. 2A) of the dielectric substrate 232. The metallization layer is then patterned (e.g., by lithography) to form resonators 234, each resonator 234 being defined by a pattern of one or more metal traces on the dielectric substrate 232. Another metallization layer can be deposited on an opposing second side (bottom side, from the perspective of FIG. 2A) of the dielectric substrate 232 to form an optional ground plane 236. An appropriate dicing technique (e.g., wafer sawing) is then performed to separate die from the wafer-level structure 206. As shown in FIG. 2B, each die corresponds to an individual RF corrosion sensor 214. The RF corrosion sensors 214 may then be integrated with a coating to form a corrosion sensing system (e.g., the corrosion sensing system 110 shown in FIG. 1) as described above.

Figure 3A:
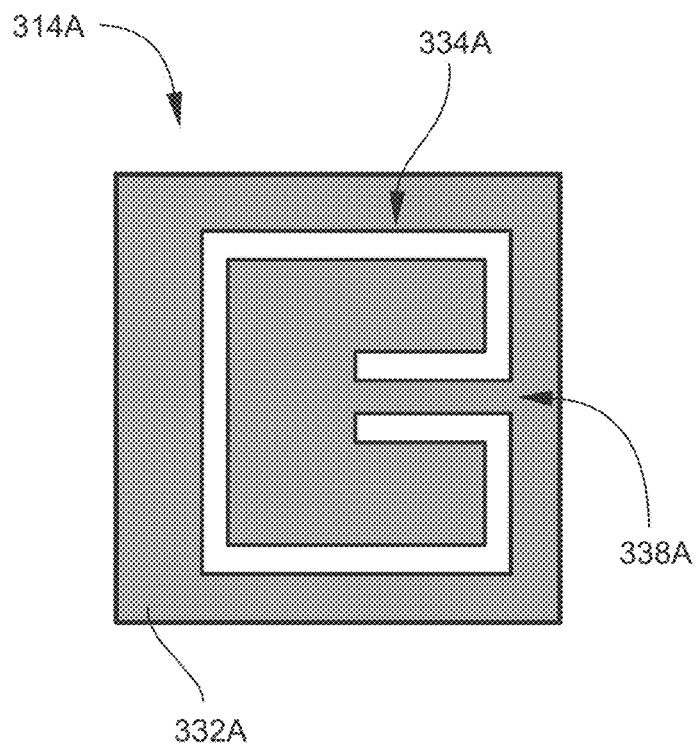
FIG. 3A is a schematic top view of an example of a radio frequency (RF) corrosion sensor according to one embodiment.

FIG. 3A is a schematic top view of an example of an RF corrosion sensor 314A according to one embodiment. FIG. 3A illustrates one non-limiting example of a resonator 334A formed by a metal trace pattern on a dielectric substrate 332A. Two ends of the metal strip are separated by a small gap and form a controlled capacitance 338A that influences the resonant frequency of the resonator 334A. When the RF corrosion sensor 314A is integrated with a coating, the controlled capacitance 338A is perturbed by the coating and thus is sensitive to changes in the coating due to corrosion. At least a portion of the resonator 334A is effective as an RF antenna capable of receiving and interacting with RF excitation signals to produce RF measurement signals.

Figure 3B:
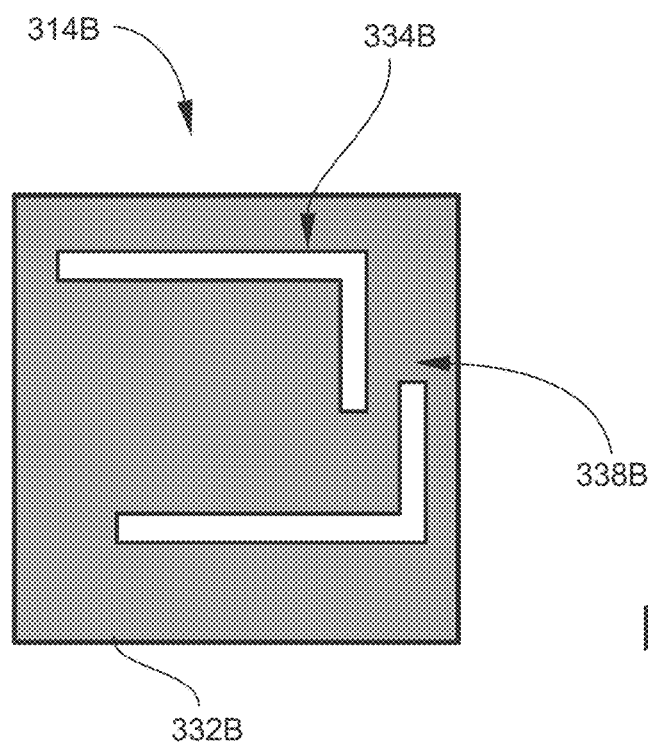
FIG. 3B is a schematic top view of an RF corrosion sensor according to another embodiment.

FIG. 3B is a schematic top view of an example of an RF corrosion sensor 314B according to another embodiment. The RF corrosion sensor 314B includes a resonator 334B formed by metal traces on a dielectric substrate 332B. Two overlapping ends of the metal traces are separated by a small gap and form a controlled capacitance 338B. Persons skilled in the art will appreciate that many variants of the configurations shown in FIGS. 3A and 3B, the materials utilized, and the fabrication techniques employed are possible.

In operation, an appropriate RF transmission device (such as may be part of the data acquisition system 120 illustrated in FIG. 1 and described further below) is operated to interrogate an RF corrosion sensor such as described above and illustrated in FIGS. 2A to 3B by transmitting an RF excitation signal to the RF corrosion sensor. The incident excitation signal may be swept through a range of RF frequencies that extend above and below the resonant frequency of the RF corrosion sensor. As the incident RF signal is swept, at frequencies near to the resonant frequency of the RF corrosion sensor, some of the RF energy will be absorbed by the RF corrosion sensor. At frequencies farther away from the resonant frequency of the RF corrosion sensor, very little if any RF energy is absorbed. This response of the RF corrosion sensor to the incident radiation may be detected by measuring, for example, the S11 signal of the RF incident signal (a well-known scattering parameter, or "S-parameter," commonly utilized in measurement of linear electrical networks). A dip (or notch, well, inverse peak) in the S11 signal can be analyzed to determine the resonant frequency and/or the Q factor of the resonance. A change in the resonant frequency and/or the Q may be evaluated to determine whether the change is an indication that the dielectric and/or conductive properties of the coating proximate to the sensor have changed in response to corrosion occurring nearby.

Figure 4:
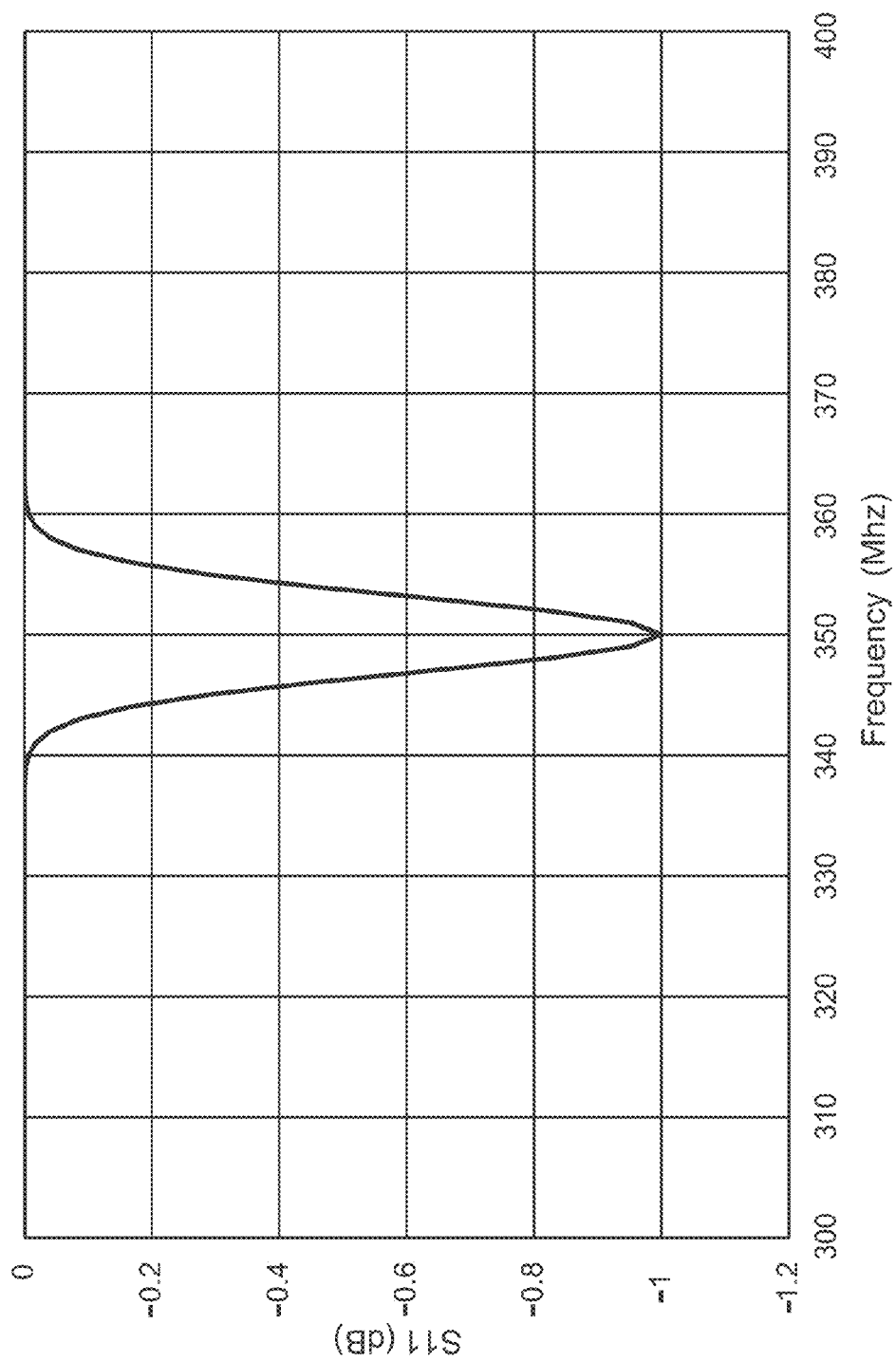
FIG. 4 is a graph of an example of a spectral response of an RF corrosion sensor as may be acquired from an RF measurement signal.

FIG. 4 is a graph of an example of a spectral response of an RF corrosion sensor as may be acquired from an RF measurement signal. Specifically, FIG. 4 is a plot of the S11 parameter (in decibels) of the RF corrosion sensor as a function of frequency (in megahertz). The spectrum includes a dip corresponding to strong absorbance by the resonator at a certain frequency (350 MHz in the illustrated example, corresponding to the local minimum of the dip).

In some embodiments, the RF corrosion sensor may have a baseline resonant frequency in a range from 100 MHz to 200 GHz, although in other embodiments the baseline resonant frequency may be above or below this range. As noted above, in certain embodiments the RF corrosion sensor may have a maximum spatial dimension of less than 50 µm. In some embodiments, an RF corrosion sensor of this scale may be configured to operate in the region around 94 GHz. The 94 GHz region is of interest for two primary reasons. First, the wavelength of 94 GHz radio waves is short (3 mm), which is believed to be feasible for self-resonance in a device scaled at less than 50 µm. Second, present commercial technologies using 94 GHz for automotive and other applications are being actively developed, which may facilitate implementation of embodiments of RF-based corrosion sensing disclosed herein.

FIGS. 5A to 7B illustrate non-limiting examples of an IR corrosion sensor according to some embodiments.

Figure 5A:
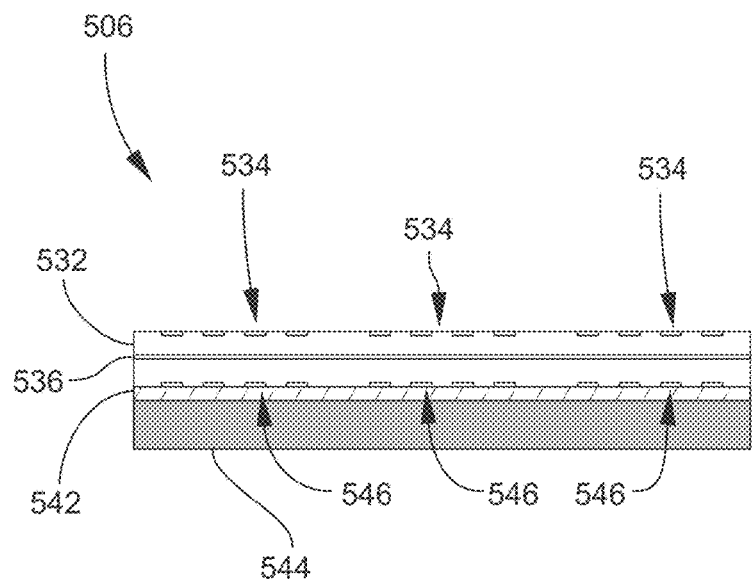
FIG. 5A is a schematic side view of an example of another wafer-level structure that may be fabricated as part of fabricating corrosion sensors according to some embodiments.
Figure 5B:
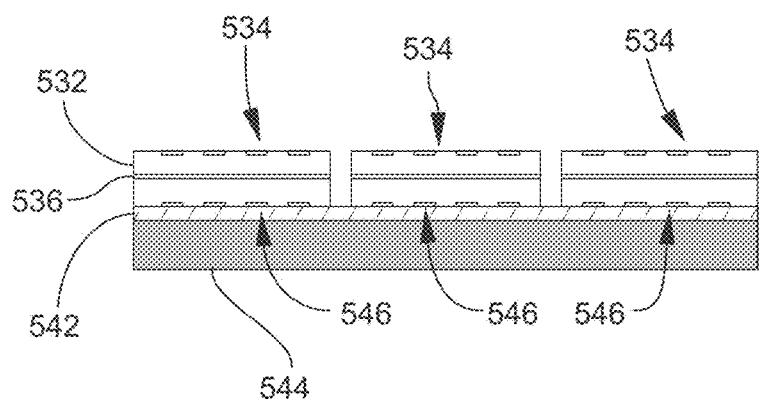
FIG. 5B is a schematic side view of the wafer-level structure illustrated in FIG. 5A after etching.
Figure 5C:
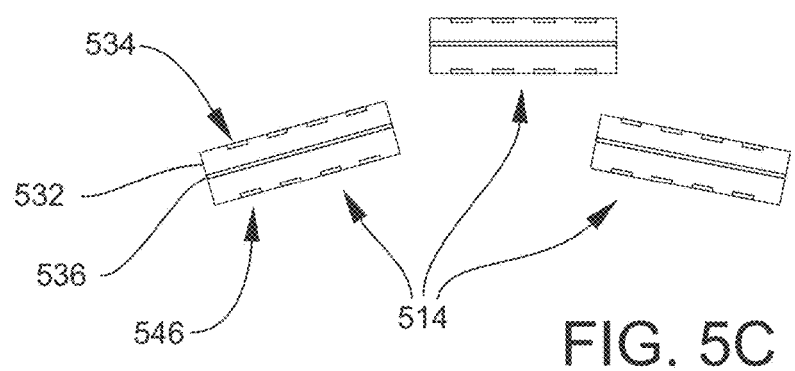
FIG. 5C is a schematic side view of an example of multiple infrared (IR) corrosion sensors released from the wafer-level structure illustrated in FIGS. 5A and 5B.

FIGS. 5A to 5C illustrate an example of fabricating IR corrosion sensors 514 in a fashion similar to the wafer-level fabrication process described above. Specifically, FIG. 5A is a schematic side view of an example of a wafer-level structure 506, FIG. 5B is a schematic side view of the wafer-level structure 506 after etching, and FIG. 5C is a schematic side view of an example of multiple IR corrosion sensors 514 released from the wafer-level structure 506. Referring to FIG. 5A, a sacrificial release layer 542 is deposited on a temporary substrate 544. The release layer 542 may have any composition suitable for its purpose as a release layer. The release layer 542 may a commercially available material such as, for example, REVALPHA® tape available from Nitto Americas, Inc., Teaneck, N.J., USA, or the 3M™ Wafer Support System available from 3M Company. A wafer-sized dielectric substrate 532 is then deposited on the release layer 542. Generally, the dielectric substrate 532 may be composed of any dielectric material suitable for IR-wavelength transmission. In some embodiments, the dielectric material may be transparent to the IR wavelengths contemplated for operation. In some embodiments an IR-reflecting material, or reflector 536, may be formed so as to be embedded in the dielectric substrate 532. For example, after forming a first layer of dielectric material on the release layer 542, a metallization layer may be deposited on the first layer of dielectric material to form the reflector 536. A second layer of dielectric material may then be deposited on the reflector 536, such that the first and second dielectric layers comprise the dielectric substrate 532 in which the reflector 536 is embedded.

Subsequently, another metallization layer is deposited on a first side (top side, from the perspective of FIG. 5A) of the dielectric substrate 532. This metallization layer is then patterned (e.g., by lithography) to form IR-responsive resonators 534, examples of which are described below.

Referring to FIG. 5B, the dielectric substrate 532 is then etched down to the release layer 542 in a pattern that defines the size and shape of the individual IR corrosion sensors 514. Any etching technique appropriate for the composition and size resolution of the materials may be employed, such as wet (chemical) etching, dry (e.g., plasma) etching. Other techniques such as laser ablation or mechanical sawing may be suitable. Referring to FIG. 5C, an appropriate release technique (thermal or laser for example) is then performed to separate individual IR corrosion sensors 514 from the wafer-level structure 506. The IR corrosion sensors 514 may then be integrated with a coating to form a corrosion sensing system (e.g., the corrosion sensing system 110 shown in FIG. 1) as described above. The approach of releasing the IR corrosion sensors 514 from a wafer level structure 506 can also be applied to the fabrication of RF corrosion sensors.

In some embodiments and as also illustrated in FIGS. 5A to 5C, the IR corrosion sensors 514 may have a double-sided configuration in which resonators are located on two opposing sides of the IR corrosion sensors 514. Specifically, each IR corrosion sensor 514 may include, in addition to the first resonator 534 on the first side of the dielectric substrate 532, a second resonator 546 on the opposing second side (bottom side, from the perspective of FIGS. 5A to 5C) of the dielectric substrate 532.

The resonator 534 (or 546) of the IR corrosion sensor 514 may be configured as a frequency-selective surface (FSS). The double-sided IR corrosion sensors 514 shown in FIGS. 5A to 5C may thus have a first FSS and a second FSS. The FSS may include a periodic array or pattern of structural features (or cells) arranged in a two-dimensional (2D) layer on the dielectric substrate 532. The structural features are sized to enable the resonator 534 to resonate at an IR wavelength. For example, each structural feature may have a characteristic dimension (e.g., length or diameter) in a range from 0.5 to 10 µm. In some embodiments, the structure of the resonator 534 may be considered as being within the class of materials known as metamaterials. In some embodiments, the IR corrosion sensor 514 may have a baseline resonant wavelength in a range from 1 µm to 15 µm, although in other embodiments the baseline resonant wavelength may be above or below this range.

Figure 6A:
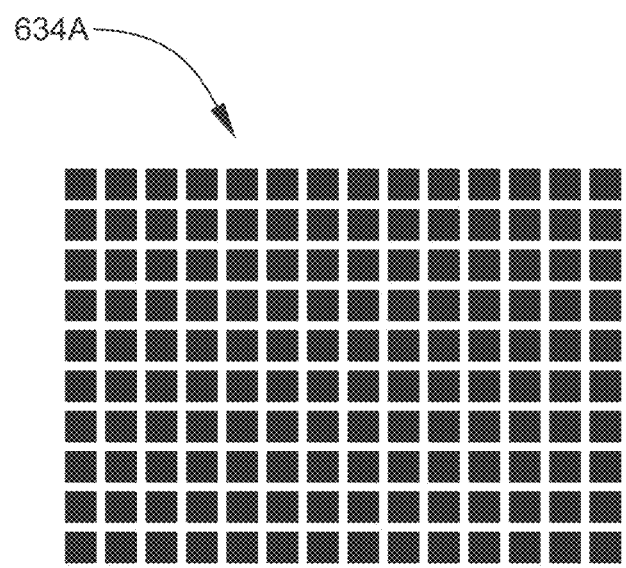
FIG. 6A is a schematic plan view of an example of a frequency-selective surface (FSS) that may be included in an IR corrosion sensor according to some embodiments.
Figure 6B:
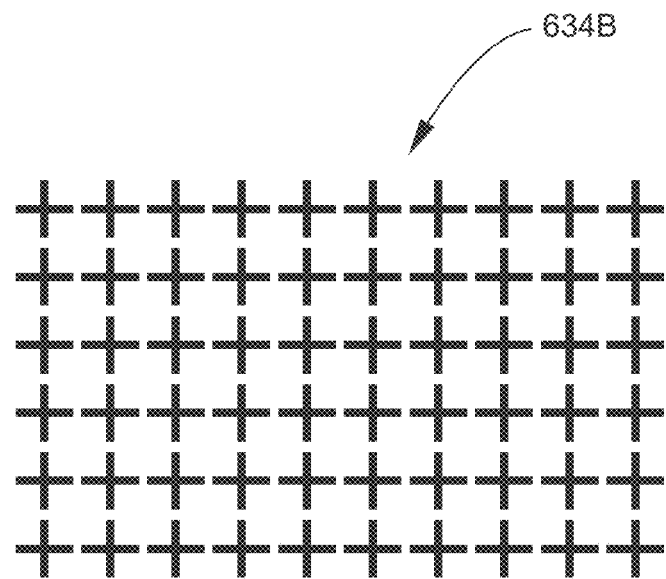
FIG. 6B is a schematic plan view of another example of an FSS that may be included in an IR corrosion sensor according to some embodiments.

FIG. 6A is a schematic plan view of an example of a frequency-selective surface (FSS) 634A that may be provided as the resonator of an IR corrosion sensor according to some embodiments. In this example, the FSS 634A includes a 2D array of metal elements or patches uniformly spaced from each other. FIG. 6B is a schematic plan view of another example of a frequency-selective surface (FSS) 634B, which includes a metal grid or mesh defining 2D array of apertures uniformly spaced from each other. In other embodiments, the 2D array and/or the periodic features need not be rectilinear. For example, an FSS may be formed by a hexagonal array of circular patches or apertures (not shown).

In operation, an appropriate IR transmission device (such as may be part of the data acquisition system 120 illustrated in FIG. 1 and described further below) is operated to interrogate an IR corrosion sensor such as described above and illustrated in FIGS. 5A to 6B by transmitting an IR excitation signal (IR beam) to the IR corrosion sensor. The resonator modulates the incident IR excitation signal, absorbing certain wavelengths while reflecting other wavelengths.

In one mode of operation, the IR excitation signal may be a broadband signal spanning a range of wavelengths that includes the wavelength corresponding to the known baseline resonant frequency of the resonator and also other wavelengths corresponding to frequency values to which the resonant frequency may be expected to have shifted due to corrosion. The modulated signal reflected back from the resonator is utilized as the IR measurement signal. The IR measurement signal may include a notch (i.e., a minimum value) corresponding to strong absorbance by the resonator of the incident IR excitation signal at a certain wavelength. The actual resonant frequency of the resonator may be determined from this IR measurement signal, and compared to the known baseline resonant frequency to determine whether corrosion has occurred in the sensing region of the corrosion sensor being interrogated.

In another mode of operation, the IR excitation signal may be centered on a specific wavelength that induces emission by the resonator of an IR measurement signal at a different wavelength. In this mode, the IR measurement signal may include a peak intensity at a certain wavelength, which likewise may be analyzed to determine a shift in resonant frequency and the occurrence of corrosion.

In either mode of operation, the provision of the reflector 536 (FIGS. 5A to 5C) in the corrosion sensor may be useful for increasing the intensity of the IR measurement signal and consequently the sensitivity of the measurement. Thus, the data acquisition system may receive the IR measurement signal directly from the resonator (via reflection or emission) or from the reflector 536.

Figure 7A:
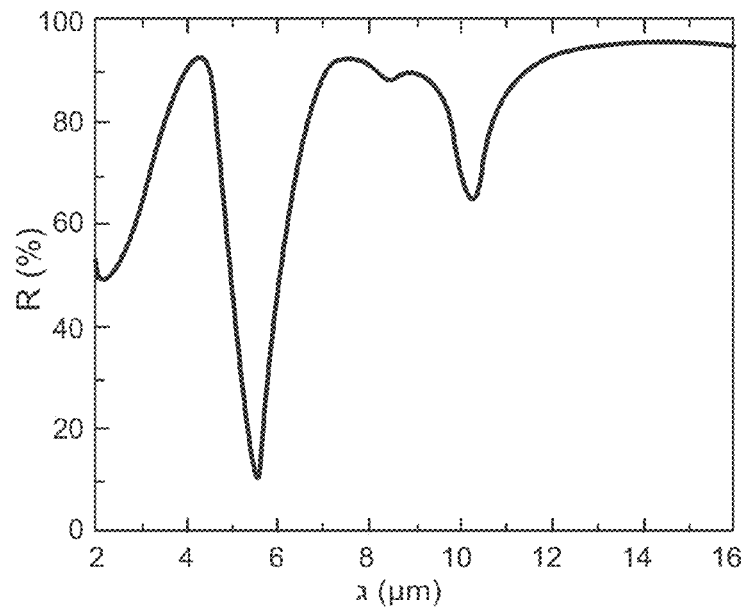
FIG. 7A is a graph of an example of a spectral response of an IR corrosion sensor according to one mode of operation, as may be acquired from an IR measurement signal.
Figure 7B:
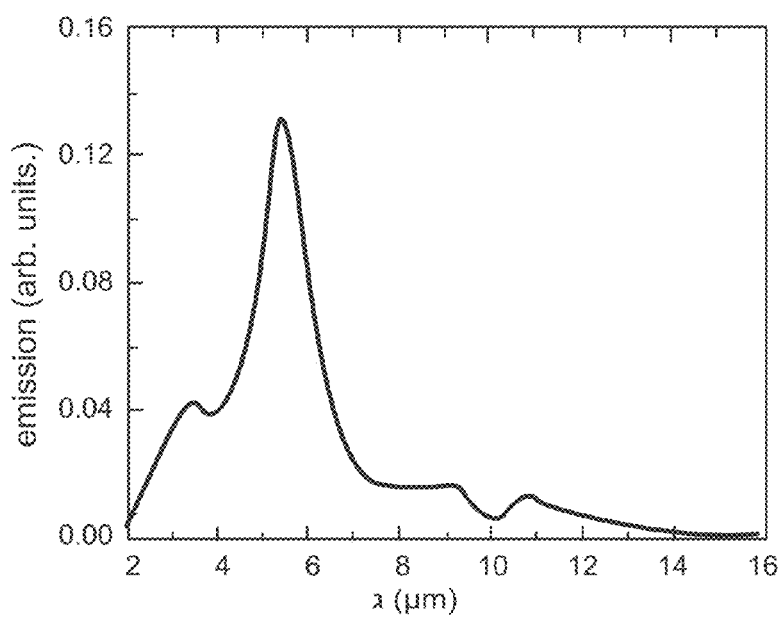
FIG. 7B is a graph of an example of a spectral response of an IR corrosion sensor according to another mode of operation.

FIG. 7A is a graph of an example of a spectral response of an IR corrosion sensor according to the first mode of operation, as may be acquired from an IR measurement signal. Specifically, FIG. 7A is a plot of reflectance (%) of the IR corrosion sensor as a function of wavelength. The spectrum includes a dip or notch corresponding to strong absorbance by the resonator at a certain wavelength. FIG. 7B is a graph of an example of a spectral response of an IR corrosion sensor according to the second mode of operation. Specifically, FIG. 7B is a plot of emission (in arbitrary units) as a function of wavelength. The spectrum includes a peak emission at a certain wavelength. Spectra such as shown in FIGS. 7A and 7B may be utilized to detect for corrosion, as described elsewhere in the present disclosure.

An IR corrosion sensor as described above may be comparatively smaller than an RF corrosion sensor, which may be considered advantageous in some applications. For example, an IR corrosion sensor may have a maximum spatial dimension of less than 10 µm. In other applications, however, an RF corrosion sensor may be preferred due to not requiring line-of-sight communication between the RF corrosion sensor and the RF probe or data acquisition system. In another aspect, the cost and complexity of the data acquisition system may influence the choice between using RF corrosion sensors or IR corrosion sensors in a given application.

Referring back to FIG. 1, in some embodiments the data acquisition system 120 includes an RF or IR excitation signal source 152, a transceiver 154 configured for transmitting RF or IR excitation signals 122 to the resonator of one or more corrosion sensors 114 and for receiving RF or IR measurement signals 124 from the resonator, and an RF or IR signal analyzer 156 configured for analyzing the measurement signal. The data acquisition system 120 may also include a computing device (or system controller) 158. FIG. 1 also schematically depicts the foregoing components enclosed in a housing 162 of the data acquisition system 120. It will be understood, however, that one or more components may be enclosed in one or more housings separate from the other components. For example, the excitation signal source 152 and the transceiver 154 may be housed together as a separate device or probe that communicates with the signal analyzer 156 via a wireless or wired communication link (such as a removable cable or tether). Such a probe may be handheld or at least portable, or may be mountable to a guide or track along with the probe is moved to enable automated scanning over a large surface area of the object 108. As another example, the computing device 158 may be a separate device that communicates with the signal analyzer 156 and/or other components via a wireless or wired communication link.

The excitation signal source 152 may be any device suitable for generating RF or IR excitation signals 122 in accordance with a given RF-based or IR-based embodiment. For example, in an RF-based embodiment the excitation signal source 152 may include an RF power source and an RF signal generator (e.g., frequency synthesizer). In an IR-based embodiment the excitation signal source 152 may be a broadband light source that emits IR radiation (e.g., various types of lamps), or a narrowband IR source such as, for example, certain types of light emitting diodes (LEDs), laser diodes (LDs), and lasers.

The transceiver 154 may be any device suitable for transmitting excitation signals 122 and receiving measurement signals 124 at the RF or IR wavelengths/frequencies contemplated for operation. For example, in an RF-based embodiment the transceiver 154 may be an RF antenna or coil. In some embodiments, separate RF antennas may be utilized for transmitting and receiving. In an IR-based embodiment the transceiver 154 includes separate devices for transmitting IR excitation signals 122 and for receiving IR measurement signals 124. The IR transmitter (or IR beam output) may simply be the output of the (IR) excitation signal source 152, or may further include optics (e.g., windows, lenses, filters, etc.) as needed or desired. The IR receiver may be an IR-sensitive photodetector.

The signal analyzer 156 may be any analytical instrument capable of measuring attributes of RF or IR signals in a manner that enables quantification of resonant frequency and/or Q and shifts in resonant frequency and/or Q associated with the corrosion sensor 114 being interrogated. The signal analyzer 156 may be an RF or IR spectrum analyzer capable of generating RF or IR spectra from RF or IR measurement signals 124 such as, for example, RF signal magnitude as a function of wavelength, IR reflectance as a function of wavelength, or IR emission as a function of wavelength. In some embodiments, the signal analyzer 156 may be a commercially available instrument. In some IR-based embodiments, the signal analyzer 156 may be a reflectance spectrometer, an IR spectrometer, a Fourier transform IR (FTIR) spectrometer, etc.

The computing device 158 may represent one or more modules (or units, or components) configured for controlling, monitoring and/or timing various functional aspects of the data acquisition system 120, such as the transmission and frequency composition of excitation signals 122, the conditioning, processing, and analysis of measurement signals 124, data logging, etc. Depending on the embodiment, all or part of the computing device 158 may be integrated with the signal analyzer 156. All or part of the computing device 158 may be, or be embodied in, for example, a desktop computer, laptop computer, portable computer, tablet computer, handheld computer, mobile computing device, personal digital assistant (PDA), smartphone, etc. The computing device 158 may include software configured to execute one or more algorithms that analyze the data encoded in received excitation signals 122, for example determining peak or dip location, amplitude, and any other information that may be utilized to determine quantitative shift in spectral response and correlate the spectral response with corrosion. In some embodiments, the computing device 158 may also be configured for providing and controlling a user interface that provides screen displays of spectral data and/or other data with which a user may interact. The computing device 158 may include one or more reading devices on or in which a tangible computer-readable (machine-readable) medium may be loaded that includes instructions for performing all or part of any of the methods disclosed herein. For all such purposes, the computing device 118 may include one or more types of hardware, firmware and/or software, as well as one or more memories and databases.

Figure 8:
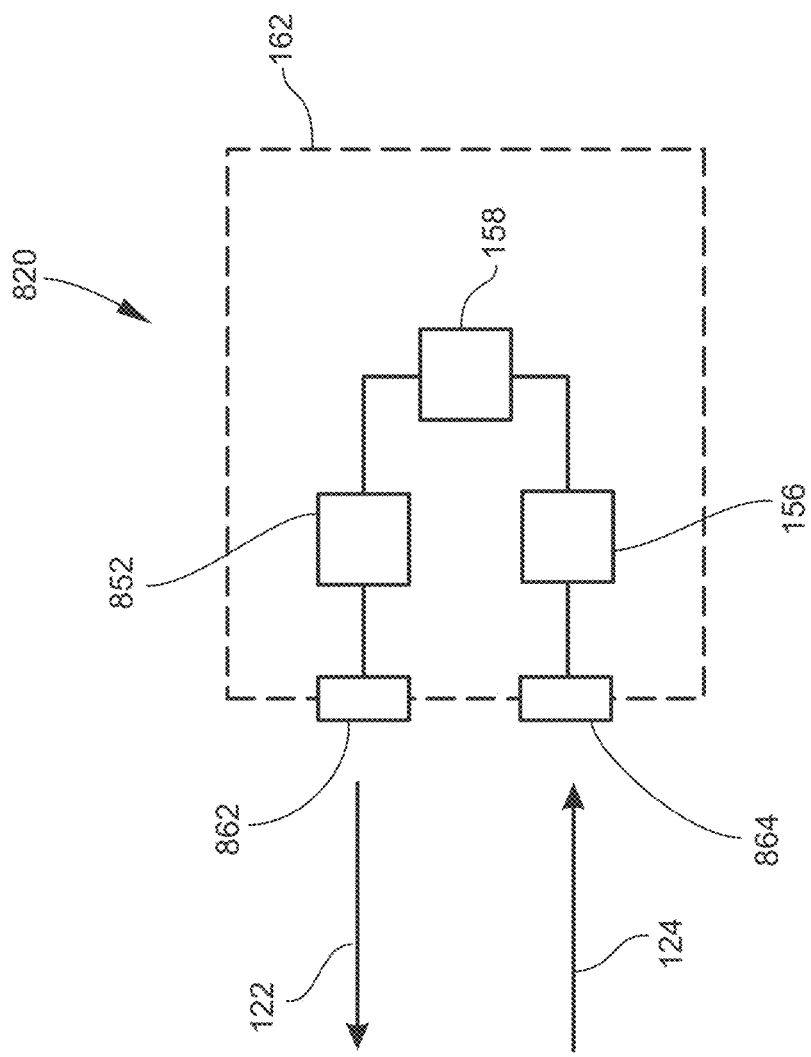
FIG. 8 is a schematic view of an example of a data acquisition system configured for IR operation according to some embodiments.

FIG. 8 is a schematic view of an example of a data acquisition system 820 configured for IR operation according to some embodiments. The transceiver includes an IR transmitter 862 and an IR receiver 864. As noted above, the IR transmitter 862 may be the output of an IR excitation signal source 852, or may be one or more separate optical components that receive the IR light generated by the IR excitation signal source 852 and direct the IR light out from the data acquisition system 820 as the IR excitation signal 122. For narrowband excitation, in some embodiments the IR excitation signal source 852 may include a plurality of light sources enabling user selection of the excitation wavelength, for example a plurality of LEDs mounted on a wheel. In other embodiments, a plurality of selectable optical filters may be provided, for example on a filter wheel. The IR receiver 864 may include one or more photodetectors.

For purposes of the present disclosure, it will be understood that terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will also be understood that when a layer (or film, region, substrate, component, device, or the like) is referred to as being "on" or "over" another layer, that layer may be directly or actually on (or over) the other layer or, alternatively, intervening layers (e.g., buffer layers, transition layers, interlayers, sacrificial layers, etch-stop layers, masks, electrodes, interconnects, contacts, or the like) may also be present. A layer that is "directly on" another layer means that no intervening layer is present, unless otherwise indicated. It will also be understood that when a layer is referred to as being "on" (or "over") another layer, that layer may cover the entire surface of the other layer or only a portion of the other layer. It will be further understood that terms such as "formed on" or "disposed on" are not intended to introduce any limitations relating to particular methods of material transport, deposition, fabrication, surface treatment, or physical, chemical, or ionic bonding or interaction. The term "interposed" is interpreted in a similar manner.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A corrosion sensor system, comprising:
a coating material; and
a corrosion sensor embedded in the coating material, the corrosion sensor comprising a dielectric substrate and a resonator disposed on the dielectric substrate, wherein:
the coating material is disposed as a coating on an object to be sensed by the sensor;
the coating material, the dielectric substrate, and the resonator define a resonant frequency of the corrosion sensor in a radio frequency (RF) range or an infrared (IR) range;
a data acquisition system configured to communicate with the corrosion sensor via RF or IR signals; and
the resonator is configured for interacting with an RF or IR excitation signal to produce an RF or IR measurement signal such that a shift in an RF or IR signal parameter determined by the data acquisition system is dependent on at least one property indicative of corrosion of the object underlying the corrosion sensor.

2. The corrosion sensor system of claim 1, wherein the dielectric substrate and the resonator have a configuration selected from the group consisting of:
the dielectric substrate and the resonator are arranged as a planar RF or IR transmission line;
the dielectric substrate and the resonator are arranged as an RLC circuit; and both of the foregoing.

3. The corrosion sensor system of claim 1, comprising an electrical ground plane on a side of the dielectric substrate opposite to the resonator.

4. The corrosion sensor system of claim 1, wherein the resonator comprises a feature selected from the group consisting of:
an RF antenna;
two or more electrically conductive sections separated by a gap and forming a capacitor; and
both of the foregoing.

5. The corrosion sensor system of claim 1, comprising a configuration selected from the group consisting of:
the resonator comprises a frequency-selective surface (FSS);
the resonator comprises a frequency-selective surface (FSS), and the FSS comprises a periodic array of structural features sized such that the FSS resonates at an IR frequency;
the resonator comprises a frequency-selective surface (FSS), and the FSS comprises a periodic array of structural features sized such that the FSS resonates at an IR frequency, wherein the structural features comprise metal elements spaced from each other or a metal grid defining apertures spaced from each other; and
the resonator comprises a frequency-selective surface (FSS), and further comprising an IR-reflecting material disposed on a side of the dielectric substrate opposite to the resonator or embedded in the dielectric substrate at a distance from the resonator, wherein the dielectric substrate comprises an IR-transmitting material.

6. The corrosion sensor system of claim 1, wherein:
the dielectric substrate comprises an IR-transmitting material, a first side, and a second side opposite the first side;
the resonator comprises a first frequency-selective surface (FSS) on the first side and a second FSS on the second side; and
the corrosion sensor further comprises an IR-reflecting material embedded in the dielectric substrate between the first FSS and the second FSS.

7. The corrosion sensor system of claim 1, wherein the corrosion sensor has a maximum spatial dimension in a range from 1 to 1000 μm.

8. The corrosion sensor system of claim 1, wherein the resonant frequency is in a range from 100 MHz to 200 GHz.

9. The corrosion sensor system of claim 1, wherein the resonant wavelength is in a range from 1 μm to 15 μm.

10. The corrosion sensor system of claim 1, comprising a plurality of corrosion sensors dispersed throughout the coating material.

11. The corrosion sensor system of claim 1, wherein plural corrosion sensors are disposed in the coating on the object.

12. The corrosion sensor system of claim 1, wherein the coating material is selected from the group consisting of:
an anti-corrosion material;
a paint;
an anti-corrosion material selected from the group consisting of epoxy, polyurethane, strontium chromate, and zinc phosphate; a liquid; a solid; and
a combination of two or more of the foregoing.

13. A corrosion detection system, comprising:
the corrosion sensor system of claim 1; and
the data acquisition system comprising an RF or IR excitation signal source, a transceiver configured for transmitting the excitation signal to the resonator and for receiving the measurement signal from the resonator, and an RF or IR signal analyzer configured for analyzing the measurement signal.

14. The corrosion detection system of claim 13, wherein the excitation source and the transceiver have a configuration selected from the group consisting of:
the excitation source comprises an RF signal generator and the transceiver comprises an RF antenna; and
the excitation source comprises an IR light source, and the transceiver comprises an IR beam output and an IR-sensitive photodetector.

15. The corrosion detection system of claim 13, wherein the corrosion sensor has a baseline wavelength-dependent parameter corresponding to an absence of corrosion in a sensing region proximate to and surrounding the corrosion sensor, and the signal analyzer is configured for:
measuring an actual wavelength-dependent parameter of the measurement signal; and
determining whether corrosion has occurred in the sensing region based on a difference between the baseline wavelength-dependent parameter and the actual wavelength-dependent parameter.

16. The corrosion detection system of claim 15, wherein the wavelength-dependent parameter is the resonant frequency, a quality factor, an RF signal magnitude as a function of frequency, an IR reflectance as a function of wavelength, or an IR emission as a function of wavelength.

17. The corrosion detection system of claim 13, wherein at least a portion of the data acquisition system comprising the transceiver is portable.

18. The corrosion detection system of claim 13, comprising a plurality of the corrosion sensors, wherein the corrosion sensors are dispersed throughout the coating material.

19. A data acquisition system for detecting corrosion of an object, the data acquisition system comprising:

a radio frequency (RF) or an infrared (IR) excitation signal source;

a transceiver configured for transmitting the RF or IR excitation signal to a corrosion sensor disposed on the object to be sensed by the corrosion sensor, and for receiving the an RF or IR measurement signal generated by the corrosion sensor in response to the RF or IR excitation signal; and an RF or IR signal analyzer configured for analyzing the measurement signal in order to determine a shift in an RF or IR signal parameter dependent on at least one property indicative of corrosion of the object underlying the corrosion sensor.

20. The data acquisition system of claim 19, wherein the excitation source and the transceiver have a configuration selected from the group consisting of:

the excitation source comprises an RF signal generator and the transceiver comprises an RF antenna; and the excitation source comprises an IR light source, and the transceiver comprises an IR beam output and an IR-sensitive photodetector.

21. The data acquisition system of claim 19, wherein the corrosion sensor has a baseline wavelength-dependent parameter corresponding to an absence of corrosion in a sensing region proximate to and surrounding the corrosion sensor, and the signal analyzer is configured for:

measuring an actual wavelength-dependent parameter of the measurement signal; and determining whether corrosion has occurred in the sensing region based on a difference between the baseline wavelength-dependent parameter and the actual wavelength-dependent parameter.

22. The data acquisition system of claim 21, wherein the wavelength-dependent parameter is a resonant frequency, a quality factor, an RF signal magnitude as a function of frequency, an IR reflectance as a function of wavelength, or an IR emission as a function of wavelength.

23. A method for detecting corrosion of an object, the method comprising:

transmitting a radio frequency (RF) or an infrared (IR) excitation signal to a corrosion sensor embedded in a coating material disposed on the object to be sensed by the corrosion sensor, wherein the corrosion sensor has a baseline wavelength-dependent parameter corresponding to an absence of corrosion of the object in a sensing region proximate to and surrounding the corrosion sensor, and the corrosion sensor interacts with the RF or IR excitation signal to produce an RF or IR measurement signal;

receiving the RF or IR measurement signal;

measuring an actual wavelength-dependent parameter of the measurement signal; and determining whether corrosion of the object has occurred in the sensing region based on a difference between the baseline wavelength-dependent parameter and the actual wavelength-dependent parameter.

24. The method of claim 23, wherein the parameter is RF signal magnitude as a function of frequency, IR reflectance as a function of wavelength, or IR emission as a function of wavelength.

25. The method of claim 23, wherein:

the corrosion sensor comprises a dielectric substrate and an RF resonator disposed on the dielectric substrate;

transmitting comprises transmitting an RF excitation signal to induce an electrical current in the resonator, wherein the RF excitation signal is modulated by the RF resonator to form an RF measurement signal; and receiving comprises receiving the RF measurement signal.

26. The method of claim 23, wherein:

the corrosion sensor comprises a dielectric substrate and an IR resonator disposed on the dielectric substrate;

transmitting comprises transmitting an IR excitation signal to the IR resonator, wherein the IR excitation signal is modulated by the IR resonator to form an IR measurement signal; and receiving comprises receiving the IR measurement signal reflected by the IR resonator.

27. The method of claim 26, wherein receiving comprises receiving the IR measurement signal reflected directly from the IR resonator, or reflected from an IR-reflecting material disposed on or embedded in the dielectric substrate.

28. The method of claim 26, wherein measuring the parameter comprises finding a wavelength at which maximum absorption of the IR excitation signal by the IR resonator occurs, or finding a wavelength at which maximum emission of the IR measurement signal by the IR resonator occurs.

29. The method of claim 23, comprising applying the coating material to the object.

* * * * *